United States Patent [19]

Pomerantzeff

[11] Patent Number: 4,710,002
[45] Date of Patent: Dec. 1, 1987

[54] MAGNIFYING OPHTHALMOSCOPE

[75] Inventor: Oleg Pomerantzeff, Brookline, Mass.

[73] Assignee: Eye Research Institute of Retina Foundation, Boston, Mass.

[21] Appl. No.: 869,853

[22] Filed: May 27, 1986

Related U.S. Application Data

[63] Continuation of Ser. No. 583,158, Feb. 24, 1984.

[51] Int. Cl.$^4$ .............................................. A61B 3/10
[52] U.S. Cl. .................................................. 351/205
[58] Field of Search ............... 351/205, 206, 207, 208; 350/138

[56] References Cited

U.S. PATENT DOCUMENTS

| | | |
|---|---|---|
| 3,475,082 | 10/1969 | Strietzel . |
| 3,582,191 | 6/1971 | Cohen et al. . |
| 3,670,097 | 6/1972 | Jones .................................... 350/138 |
| 3,825,328 | 7/1974 | Hoch .................................... 350/138 |
| 3,945,712 | 3/1976 | Crock et al. . |
| 3,963,329 | 6/1976 | Stumpf et al. . |
| 4,015,898 | 4/1977 | Schrimer .......................... 351/205 X |
| 4,248,505 | 2/1981 | Muchel et al. . |

OTHER PUBLICATIONS

K. E. Schirmer, "The Upright Fundus Image in Indirect Opthalmoscopy", Arch Opthal., vol. 77, Jan. 1967, pp. 67–70.

*Primary Examiner*—Rodney B. Bovernick
*Attorney, Agent, or Firm*—Lahive & Cockfield

[57] ABSTRACT

A stereoscopic ophthalmoscope for use with a condensing lens to observe the fundus of a patient's eye, the ophthalmoscope having a left eyepiece and a right eyepiece, a light source for directing light into the patient's eye so that an image of the patient's eye is focused by the condensing lens in a focal plane perpendicular to an optical axis, the ophthalmoscope having the improvements consisting of an image-splitting device for splitting the image into a left image and a right image travelling along a left optical path and a right optical path, respectively, left and right image-rotating devices arranged in optical alignment with the image-splitting device for inverting and reversing each of the left and right images from the image-splitting device, and left and right magnifying devices, each including an objective lens and an ocular lens and each arranged in optical alignment with the respective image-rotating devices to magnify the image therefrom and to transmit that image to the respective eyepiece.

10 Claims, 6 Drawing Figures

MAGNIFYING OPHTHALMOSCOPE

This application is a continuation of application Ser. No. 583,158, filed Feb. 24, 1984.

BACKGROUND OF THE INVENTION

This invention relates to ophthalmological instruments and, in particular, to ophthalmoscopes which permit examination, under magnified conditions and proper stereopsis, of the fundus or retina of a patient's eye.

A number of instruments are known for examination of the fundus of the eye. The direct ophthalmoscope is typically a hand-held instrument which illuminates but does not actually magnify the fundus. Because no lenses are employed in a direct ophthalmoscope, other than those which correct for the patient's corneal refraction, the image is erect rather than inverted. An appearance of magnification, known as physiological magnification, occurs in the direct ophthalmoscope because the image of the patient's fundus is larger than expected by the observer. However, since the fundal image is focused by only one of the examining practitioner's own eyes, the view lacks depth.

An indirect ophthalmoscope, on the other hand, uses a magnifying lens, called a condensing or observation lens. This lens is placed in front of the patient's eye and is used to focus a magnified image of fundus between the patient and the observer for stereo viewing. The condensing lens typically is used in conjunction with a binocular device, supported upon the practitioner's head, which serves to reduce the practitioner's interpupilliary distance and provide illumination. The fundal image viewed by the practitioner is inverted and reversed.

Although they produce inverted and reversed images, indirect ophthalmoscopes have gained widespread recognition as diagnostic tools in identifying diseases such as tumors, diabetic retinopathy, retinal detachments and peripheral uveitis. Magnification in the indirect ophthalmoscope is dependent upon the power of the condensing lens. Even though the image viewed by the practitioner with an indirect ophthalmoscope is inverted and reversed, the indirect ophthalmoscope maintains proper stereopsis because the images seen by the left and right eyes of the practitioner are also switched by the instrument. Hence, normal depth perception is reinstated. If the left and right images were not also switched, a condition known as pseudostereopsis would exist in which protuberances appear as cavities, etc.

Despite the advantages of indirect ophthalmoscopes, there exists a need for ophthalmoscopes with better magnification, and with good resolution, particularly to study the fine details around the macula of the eye and to examine tiny lesions. Such instruments desirably provide better magnification without sacrificing proper stereopsis and without sacrificing substantial portion of the field of view so that depth perception is maintained and nearly the entire fundus can be examined.

SUMMARY OF THE INVENTION

The present invention resides in an improved indirect ophthalmoscope providing magnified stereo images of a patient's eye fundus. The instrument has a pair of magnifying (Keplerian) telescopes and a series of image-rotating mirrors which transmit the fundal image to the magnifying optics. This instrument both achieves magnification and maintains stereopsis, without significant losses in either illumination or field of vision. In a preferred embodiment, the ophthalmoscope is a compact, headworn, diagnostic instrument for use with a conventional condensing lens to provide fundal images to the practitioner.

In conventional indirect ophthalmoscopes, magnifying power is limited by the hand-held condensing lens. A condensing lens will magnify not only the image seen by the practitioner but also the image of the light source in the patient's pupillary plane. A limit is reached either when the magnified image of the light source leaves no room in the patient's pupil for the practitioner to observe the fundal image, or when the light source is partially cut by the patient's iris thereby reducing the brightness of the fundal image. Practically this limit is $5\times$. The present invention solves this problem by incorporating telescopes into the ophthalmoscope eyepieces, in a manner that increases magnification of the fundal images without affecting the magnification of the light source.

An opthalmoscope according to a preferred embodiments of the invention employs Keplerian rather than Galilean telescopes. Keplerian magnifying optics provide a significantly larger field of vision to the practitioner. Such a Keplerian system (i.e., having positive oculars) with $6\times$ magnification yields a field of view of about 42 degrees, and a similar $10\times$ Keplerian system yields a field of about 33 degrees. In comparison, a Galilean system (i.e., having negative oculars) would yield only about an 8 degree field under $6\times$ magnification.

Because the Keplerian telescopes incorporated into each eyepiece create inverted, reversed images in the observer's eyes, the practitioner would see an erect image of the fundus if the magnifying optics and condensing lens were used alone in a conventional arrangement. However, since the condensing lens acts first to interchange the right and left images of the practitioner's pupils the erect images of the fundus would be seen by the practitioner with psendosteropsis. To restore the stereopsis, the images focused in the left and right eyepieces must be interchanged again or the images of the fundus must be once more reversed and inverted.

The present invention solves this problem by providing Keplerian magnifiying subassemblies and a cooperating image-rotating subassembly (preferably two such image-rotating subassemblies, operating in tandem on the left and the right images) to reinvert and reverse the images. The net result is that the practitioner again sees an inverted and reversed image (as normally the case with indirect ophthalmoscopes) and, moreover, it is seen with proper stereopsis and under magnified conditions.

In one preferred embodiment, the opthalmoscope includes left image and a right image rotating subassembly, each composed of a series of four mirrors arranged in optical alignment to invert and reverse the image. In this embodiment, the leading mirrors of the two subsystems are also arranged to serve as a beam splitting device to separate the image into left and right views. At the other end of the subsystems, the last mirrors in each series transmit their images to the left and right objective lenses, respectively, of the two magnifying subsystems. As shown in FIG. 3, the beam splitting and the image-rotating elements operate without image interchange, i.e., without left-right interchange.

In addition, the invention can include a mechanism for adjusting the position of the leading mirrors to match the practitioner's interpupilliary and observation distances. Moveover, the invention can include a means for adjusting the angle of the illuminating light and the degree of magnification. In one preferred embodiment, the location of the objective lenses also is adjustable by a mechanism to provide so-called "zoom" focusing control.

The preferred embodiments of the invention will next be described in detail; however, it should be clear that various changes and modifications may be made by those skilled in the art without departing from the spirit or scope of the invention. For example, various other devices besides the specific arrangement of mirrors shown can be employed to rotate the image received from the condensing lens before it is passed to the magnifying optics. Similarly, a single image inverting subsystem can be employed before the beam is split into left and right images. Moveover, various equivalent mechanisms can be constructed to replace the adjustment mechanisms (e.g., cam mechanisms, pivoting mechanisms and translation stages) described hereinafter.

BRIEF DESCRIPTION OF THE DRAWINGS

FIG. 5 is a bottom view of the zoom control knob for the instrument of FIGS. 4 and 4a.

DETAILED DESCRIPTION OF THE PREFERRED EMBODIMENTS

Figure 1:
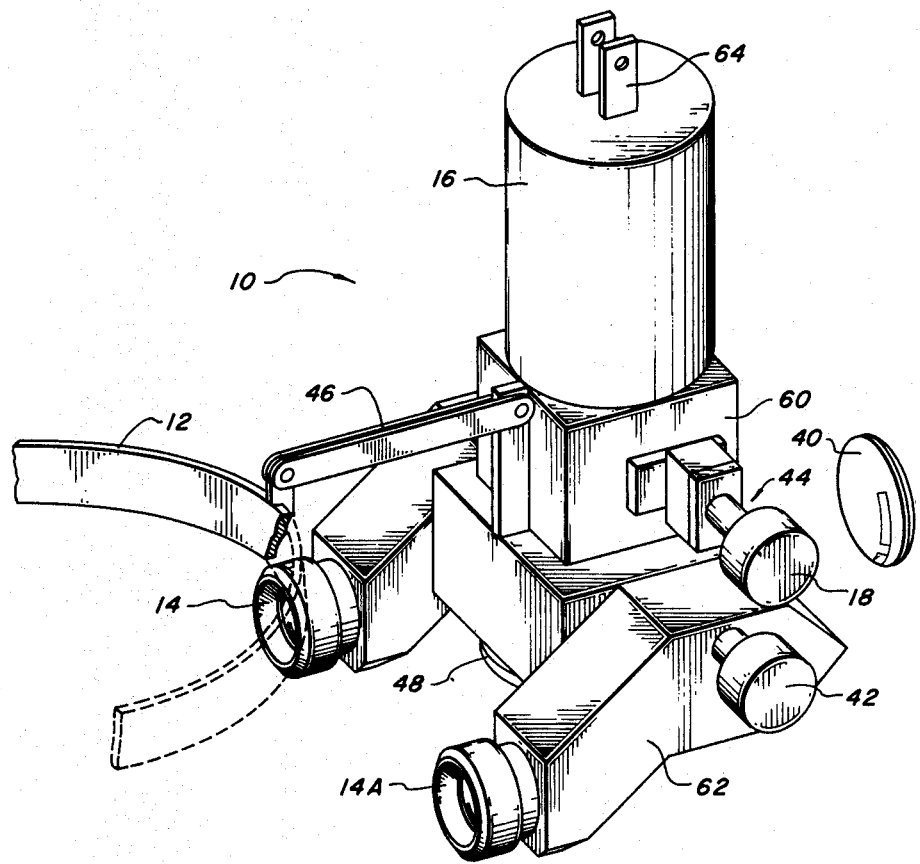
FIG. 1 is an overall, perspective view of an ophthalmoscope according to the present invention.

FIG. 1 shows an overall view of an ophthalmoscope 10 according to the invention and having a hand-held condensing lens 40 and an instrument 60 adapted to be worn on a practitioner's head. The instrument 60 includes a headband 12 and a support bracket 46 which holds the lamp body 16 and the optical viewing assembly 62 in front of the practitioner. The instrument 60 also includes an aperture 44 (through which images are received) and eyepieces 14 and 14a for binocular viewing. Additionally, the instrument 60 includes an adjustment knob 18 for adjusting the angle of illumination and another adjustment knob 42 to adjust for the size of the patient's pupil as well as a zoom control 48 to adjust the magnification. Electrical connector 64 provides the electrical contacts for a battery (not shown).

Figure 2:
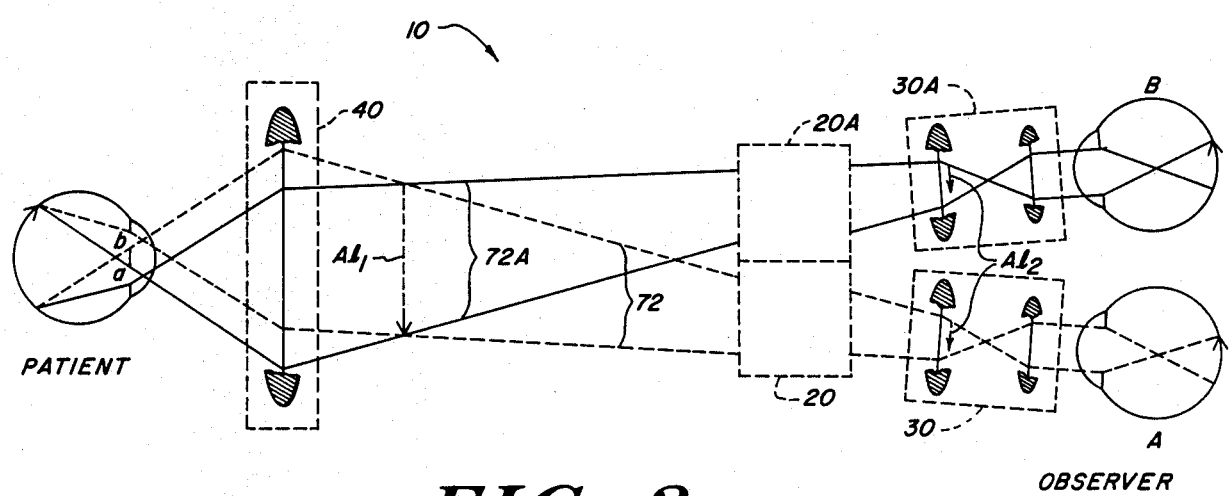
FIG. 2 is a schematic drawing of the imaging optics of the opthalmoscope of FIG. 1.

In FIG. 2 the optical imaging path is shown schematically. A left optical path 72, shown by dotted lines, is defined by the condensing lens 40, a left image-rotating subassembly 20, and a left magnifying subassembly 30. A right optical path 72A, shown in solid lines is defined by condensing lens 40, a right image-rotating subassembly 20A and a right magnifying subassembly 30A. Condensing lens 40 focuses an image of the patient's fundus in air at focal plane $Al_1$. This image is inverted, top to bottom and left to right. Note that the entrance windows of the practitioner's pupils, "a" and "b" in FIG. 2, in the patient's pupilliary plane also are interchanged by the condensing lens 40 so that the practitioner's left eye "A" looks through the right entrance window "a" and vice versa. Subassemblies 20 and 20A split the image rays from the condensing lens 40 into left and right views and pass them to the magnifying subassemblies 30 and 30A. In order to avoid the condition of pseudostereopsis created because the image is refocused at focal planes $Al_2$ by the magnifying subassemblies 30 and 30A, the intermediate subassemblies 20 and 20A reinvert the image $Al_2$ to comform to what it is in focal plane $Al_1$. The end result seen by the practitioner is thus a magnified, inverted image with proper stereopsis. The intermediate subassemblies 20 and 20A are known generically as image rotators and are preferably implemented by mirrors, although other elements such as prisms or combinations of prisms and mirrors can be employed.

Figure 3:
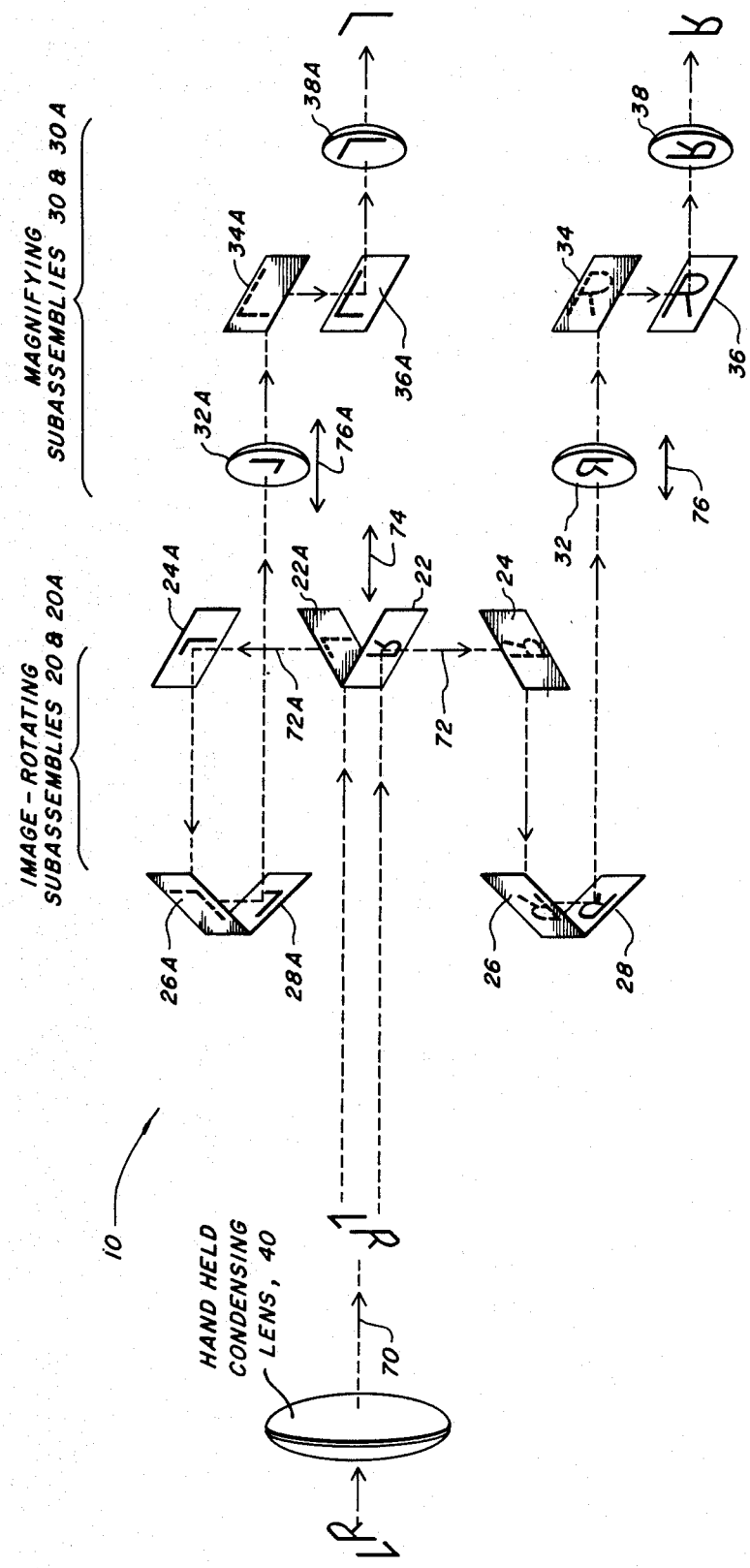
FIG. 3 is a more detailed schematic drawing of the optical components of the opthalmoscope of FIG. 1.

In FIG. 3 the preferred optical arrangement for the viewing assembly 62 of FIG. 1 is shown in detail. FIG. 3 also provides additional details on the elements shown schematical in FIG. 2. In FIG. 3 the image rotators 20 and 20A of FIG. 2 are each formed by a series of four mirrors 22, 24, 26, 28 and 22A, 24A, 26A, 28A. The first mirrors 22, 22A in each series serve to split the inverted image from the condensing lens 40 into left and right images. The position of mirrors 22 and 22A is adjustable forward and rearward along the optical axis 70 as shown by arrow 74 to match the patient's pupil size by the adjustment knob 42 shown in FIG. 1 using a rack and pinion drive or the like.

The left and right images reflected from first mirrors 22 and 22A are then reflected further by mirrors 24, 26, 28 and 24A, 26A, 28A, respectively, which sequentially rotate each image 180 degrees both up-to-down and left-to-right.

The images from the mirrors 28 and 28A, respectively, in each of the left and right image-rotating subassemblies, are transmitted to the left and right magnifying subassemblies 30 and 30A which each include objective lenses 32, 32A and ocular lenses 38, 38A, respectively. Intermediate between the objective and ocular lenses of each magnifying subassembly are first and second periscopic mirrors 34, 36 and 34A, 36A, respectively which provide a further separation between the objective and ocular lenses of each assembly without sacrificing the overall compactness of the instrument.

Figure 4:
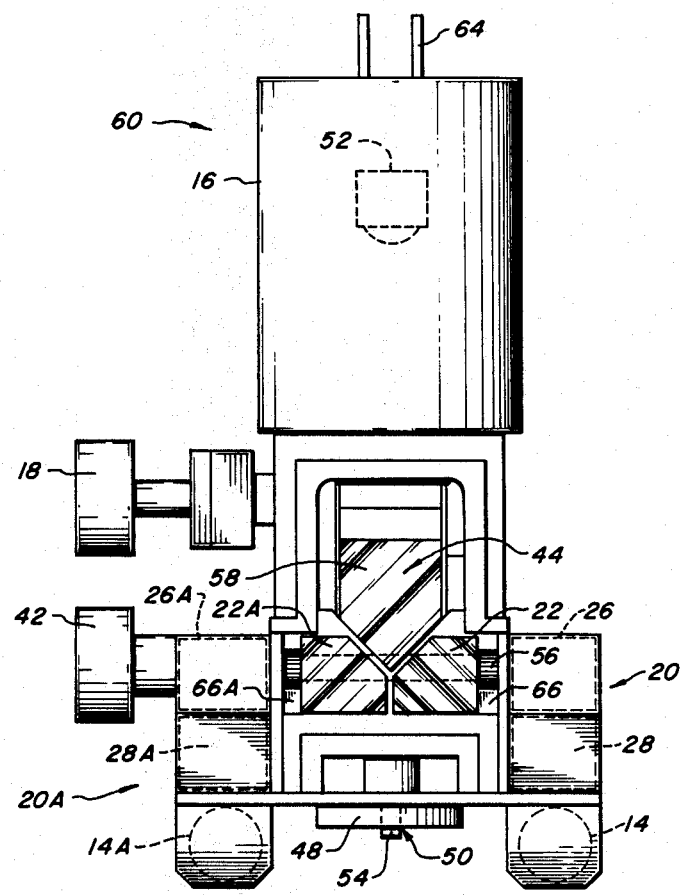
FIGS. 4 and 4a are front and side views, respectively, of the body of an ophthalmoscopic instrument for use with a condensing lens according to the present invention.
Figure 5:
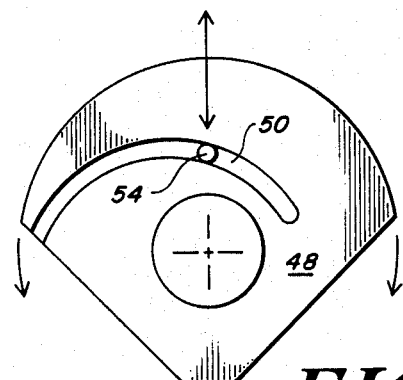

The positions of the objective lenses 32 and 32A relative to their respective ocular lenses 38 and 38A can be adjusted forward and rearward along the left and right optical paths as shown by arrows 76 and 76A using the zoom control 48 shown in FIGS. 4 and 5. In one embodiment, the control 48 is a disc-shaped knob carrying a spiral groove into which is inserted a pin attached by a rack to both objective lenses 32 and 32A. Turning the knob thus provides a cam mechanism to translate the position of the objective lenses 32 and 32A fore and aft. Additionally, in the preferred embodiment the ocular lenses 38 and 38A are individually adjustable, (e.g., by rotation in a threaded housing) to match the practitioner's refraction and thus provide sharper focus.

Figure 4A:
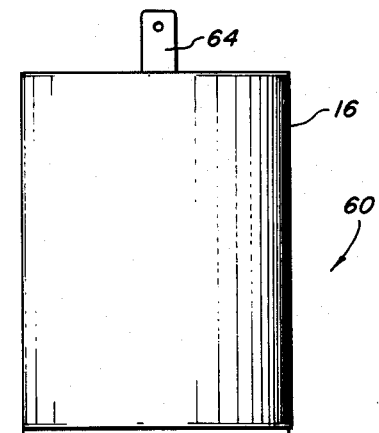
Figure 4A:
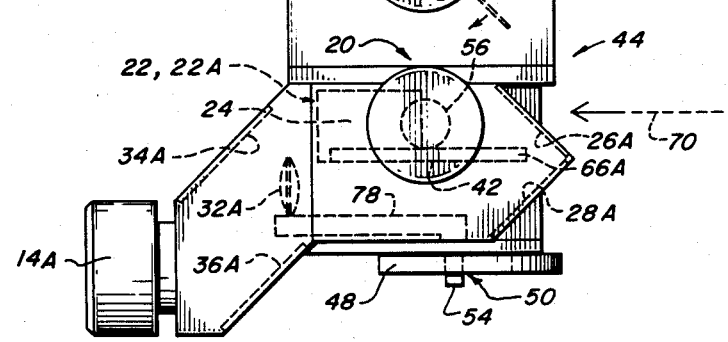

FIGS. 4 and 4a show that the lamp body 16 of the instrument 60 of FIG. 1 houses a lamp 52 which can be connected to a conventional battery pack (not shown) via electrical plug 64. When the lamp is on, light is reflected off the illumination mirror 58 out of aperture 44 to the condensing lens (FIG. 3) and from there to the inside of the patient's eye. The angle of the illumination mirror 58 is adjusted by knob 18; rotation of knob 18 causes mirror 58 to pivot about a horizontal axis transverse to the optical axis 70.

Image rays returning from the patient's eye pass back through the condensing lens and upon entering aperture 44 are split by the first image rotating mirrors 22 and 22A into the left and right images which are manipulated and passed to the eyepieces as discussed above. Knob 42 is connected to a pinion gear 56 which engages two racks 66, 66A across which are seated the first mirrors 22 and 22A. Rotation of knob 42 activates the rack and pinion mechanism and causes mirrors 22, 22A to move forward or backward.

The zoom control of objective lenses 32 and 32A is shown in FIGS. 4 and 4a and particularly in FIG. 5. Knob 48 or the bottom of the instrument carries a spiral groove 50 into which pin 54 is inserted. Pin 54 is connected to a rack 78 upon which the objective lenses 32 and 32A are seated. Rotation of knob 48 displaces pin 54 and rack 78 thus causing the objective lenses 32 and 32A to move forward and back.

What is claimed is:

1. A stereoscopic ophthalmoscope for use with a condensing lens to observe the fundus of a patient's eye, the ophthalmoscope having a left eyepiece and a right eyepiece, a light source and a means for directing light from the light source into the patient's eye whereby a single image of the patient's eye is focused by the condensing lens in a focal plane perpendicular to an optical axis, said ophthalmoscope having the improvement comprising
   A. an image-splitting means for splitting the single image, without interchange into a left image and a right image travelling along a left optical path and a right optical path, respectively,
   B. left and right image-rotating means, each arranged in optical alignment with said image splitting means, for inverting and reversing each of the left and right images from the image-splitting means, and
   C. left and right magnifying means, each comprising an objective lens and an ocular lens and each arranged in optical alignment with the respective image rotating means to magnify the image therefrom and to transmit that image to the respective eyepiece, whereby said eyepieces present to an observer a stereoscopic, magnified view of said fundus, inverted and with proper stereopsis.

2. An ophthalmoscope according to claim 1 wherein said image-splitting means further comprises a V-shaped reflecting means centrally positioned along the optical axis.

3. An ophthalmoscope according to claim 1 wherein each image-rotating means further comprises a succession of optically-aligned reflecting means for stepwise rotation of the image to an inverted, reversed state.

4. An ophthalmoscope according to claim 1 wherein each magnifying means further comprises a pair of periscopic reflecting means arranged in optical alignment between the objective lens and the ocular lens.

5. An ophthalmoscope according to claim 1 having the further improvement comprising means for adjusting the position of the image-splitting means along the optical axis.

6. An ophthalmoscope according to claim 1 wherein the means for directing light comprises means for adjusting the angle along which the light is directed.

7. The ophthalmoscope of claim 1 wherein said magnifying means includes means for adjusting the positions of the objective lenses along their respective optical paths.

8. An ophthalmoscopic apparatus having a left eyepiece and a right eyepiece, a light source and a means for directing light from the light source into a patient's eyes to illuminate a single image of the patient's eye, said apparatus having the improvement comprising
   A. an image-splitting means for splitting the single image into a left image and right image,
   B. left and right image-rotating means, each arranged in optical alignment with said image-splitting means, for inverting and reversing each of the left and right images from the image-splitting means, said image-splitting and image-rotating means providing said image splitting, inverting, and reversing without image interchange, and
   C. left and right magnifying means, each comprising an objective lens and an ocular lens, and each arranged in optical alignment with the respective image-rotating means to magnify the image therefrom and transmit that image to the respective eyepiece, whereby said eyepieces when used with a condensing lens present to an obeserver a stereoscopic, magnified view of said fundus, inverted but with proper stereopsis.

9. A stereoscopic ophthalmoscope for use with a condensing lens to observe the fundus of a patient's eye, the ophthalmoscope having a left eyepiece and a right eyepiece, a light source and a means for directing light from the light source into the patient's eye whereby a single image of the patient's eye is focused by the condensing lens in a focal plane perpendicular to an optical axis, said ophthalmoscope having the improvement comprising
   A. an adjustale iimage-splitting means for splitting the single image, without interchange into a left image and a right image travelling a left optical path and a right optical path respectively, the image-splitting means comprising a V-shaped reflecting means centrally positioned along the optical axis and adapted for movement in the forward and rearward directions along the optical axis,
   B. left and right image-rotating means each arranged in optical alignment with the image-splitting means for inverting and reversing the left and right images from the image-splitting means without interchanging said images, the image-rotating means further comprising a series of reflecting means arranged in optical alignment for rotating the image stepwise until an inverted, reversed image is obtained,
   C. left and right magnifying means, each comprising an adjustable objective lens and an ocular lens, arranged in optical alignment with their respective image-rotating means to magnify the images therefrom and transmit them to the respective eyepieces, the magnifying means further comprising a pair of left and right periscopic reflecting means, each pair arranged between the objective lens and the ocular lens of their respective magnifying means, and the magnifying means also comprising a means for adjusting the positions of the objective lenses forward and rearward in relation to their respective ocular lenses, and
   D. a means for adjusting the angle of light directed from the light source into the patient's eye, whereby an observer viewing said fundus through said eyepiece will see a stereoscopic, magnified view of said fundus, inverted but with proper stereopsis.

10. A method for examining the fundus of a patient's eye with a light source and a condensing lens, said method comprising the steps of
   A. directing light from the light source into the patient's eye,
   B. condensing an image of the fundus of the patient's eye in a focal plane perpendicular to an optical axis defined by the condensing lens placed before the patient,
   C. splitting the image from the condensing lens, without interchange into a left image and a right image,
   D. rotating each of the split left and right images such that each image is inverted and reversed,
   E. magnifying the rotated images in a pair of magnifying means, and
   F. focusing said rotated images at an image plane, thereby to present a stereoscopic, inverted, magnified view of the fundus of the patient's eye.

* * * * *